(12) United States Patent
Norwood et al.

(10) Patent No.: US 10,351,491 B2
(45) Date of Patent: Jul. 16, 2019

(54) PROCESS FOR RECOVERING PARAXYLENE FROM AT LEAST TWO FEEDSTREAMS CONTAINING XYLENE ISOMERS

(71) Applicant: BP Corporation North America Inc., Naperville, IL (US)

(72) Inventors: Steven Norwood, Athens, AL (US); Chyau Lin, Shanghai (CN); Jeffrey Amelse, Batavia, IL (US); Scott Roberts, Naperville, IL (US); Richard Wilsak, Naperville, IL (US); Brian Slusar, Winfield, IL (US)

(73) Assignee: BP Corporation North America Inc., Houston, TX (US)

( * ) Notice: Subject to any disclaimer, the term of this patent is extended or adjusted under 35 U.S.C. 154(b) by 87 days.

(21) Appl. No.: 14/777,077

(22) PCT Filed: Mar. 14, 2014

(86) PCT No.: PCT/US2014/027705
§ 371 (c)(1),
(2) Date: Sep. 15, 2015

(87) PCT Pub. No.: WO2014/152762
PCT Pub. Date: Sep. 25, 2014

(65) Prior Publication Data
US 2016/0031772 A1    Feb. 4, 2016

Related U.S. Application Data
(60) Provisional application No. 61/794,401, filed on Mar. 15, 2013.

(51) Int. Cl.
C07C 7/14    (2006.01)
C07C 7/12    (2006.01)

(52) U.S. Cl.
CPC . C07C 7/14 (2013.01); C07C 7/12 (2013.01)

(58) Field of Classification Search
None
See application file for complete search history.

(56) References Cited

U.S. PATENT DOCUMENTS 2,810,772 A    10/1957 Bennett et al.
2,827,503 A    3/1958 Kennel et al.
(Continued)

FOREIGN PATENT DOCUMENTS

JP    S49-15681    2/1774
JP    H10-502330    3/1998
(Continued)

*Primary Examiner* — Tam M Nguyen
(74) *Attorney, Agent, or Firm* — McDonnell Boehnen Hulbert & Berghoff LLP

(57) ABSTRACT

Processes for recovering paraxylene from at least two feedstreams containing xylene isomers. The process includes directing to a paraxylene recovery zone comprising at least one crystallization zone, a paraxylene-lean feedstream having a paraxylene to total xylene isomer ratio of 0.50 or less, and also directing to the paraxylene recovery zone, a paraxylene-rich feedstream having a paraxylene to total xylene isomer ratio of greater than 0.50. A paraxylene-containing product stream is recovered from the paraxylene recovery zone having a paraxylene to total xylene isomer ratio greater than that of the paraxylene-rich feedstream. The process provides improvements in paraxylene recovery efficiency and/or cost effectiveness.

47 Claims, 4 Drawing Sheets

(56) References Cited

U.S. PATENT DOCUMENTS

| | | |
|---|---|---|
| 4,393,266 A | 7/1983 | Smolin |
| 5,329,060 A | 7/1994 | Swift |
| 5,329,061 A * | 7/1994 | Swift .................. C07C 7/14 585/805 |
| 5,448,005 A | 9/1995 | Eccli et al. |
| 6,147,272 A | 11/2000 | Mikitenko et al. |
| 6,565,653 B2 | 5/2003 | Wilsak |
| 7,405,340 B2 | 6/2008 | Amelse |
| 8,252,967 B2 | 8/2012 | Hagemiester et al. |
| 2002/0065444 A1 | 5/2002 | Deckman et al. |
| 2008/0249345 A1 | 10/2008 | Kinn et al. |
| 2014/0336436 A1* | 11/2014 | Bender ................ C07C 7/13 585/821 |

FOREIGN PATENT DOCUMENTS

| | | |
|---|---|---|
| RU | 2167139 | 5/2001 |
| WO | WO-2005/100287 | 10/2005 |
| WO | WO-2010/019342 | 2/2010 |

* cited by examiner

PROCESS FOR RECOVERING PARAXYLENE FROM AT LEAST TWO FEEDSTREAMS CONTAINING XYLENE ISOMERS

BACKGROUND OF THE INVENTION

The disclosure relates generally to processes for recovering paraxylene from at least two feed streams containing xylene isomers, particularly the integration of recovery of paraxylene from a paraxylene-lean feedstream and a paraxylene-rich feedstream. More specifically, the disclosure relates to processes incorporating the use of a paraxylene recovery zone comprising at least one crystallization zone, and optionally at least one reslurry zone.

Paraxylene (p-Xylene or pX), in purified form, is useful for making terephthalic acid. Paraxylene is generally obtained by separation from Mixed Xylenes. In the industry, Mixed Xylenes refer to a narrow boiling distillation heart cut of the C8 aromatics comprising the three xylene isomers orthoxylene (oX), metaxylene (mX) and paraxylene (pX), as well as ethylbenzene (EB). Mixed Xylenes may also contain non-aromatic compounds with boiling points close to the xylenes. These mainly comprise C9 paraffins and naphthenes. Mixed Xylenes generally also contain low levels of toluene and C9 and higher aromatics present due to their imperfect separation in the distillation towers used to produce the Mixed Xylenes heart cut. ASTM publishes a Standard Specification for Xylenes for Paraxylene Feedstock (ASTM D 5211-07 or subsequent versions); however, specifications that deviate from this are often set between Mixed Xylenes purchasers and suppliers.

The proportions of xylene isomers and ethylbenzene present in Mixed Xylenes will vary depending upon the source of the Mixed Xylenes. Mixed Xylenes are typically a narrow boiling distillation cut obtained from a reformate of the refinery catalytic reformer unit or another unit used to produced Mixed Xylenes, such as a non-selective toluene disproportionation (TDP) unit, a selective toluene disproportionation (STDP) unit, a non-selective or selective toluene alkylation unit, a toluene/aromatic C9-plus transalkylation (TA) unit or an aromatic C9-plus transalkylation unit. Toluene alkylation units react toluene with methanol to produce xylene isomers and water, although other side reactions can take place, such as the conversion of part of the methanol to alkanes, olefins and other alkylation products. Processes for producing Mixed Xylenes may be "selective" or "non-selective" processes. A non-selective process generally produces xylene isomers with a near equilibrium distribution of the xylene isomers (paraxylene:metaxylene: orthoxylene) of approximately 1:2:1, i.e. the ratio of paraxylene to total xylene isomers is approximately 0.25. In contrast, a process that is selective for paraxylene yields a paraxylene concentration above the theoretical equilibrium, i.e. the ratio of paraxylene to total xylene isomers is greater than 0.25. Thus, xylenes produced in catalytic reformers, conventional TDP units, conventional (non-selective) toluene alkylation units, and toluene/aromatic C9-plus or aromatic C9-plus transalkylation units generally contain xylene isomers with a near equilibrium distribution (i.e. with a ratio of paraxylene to total xylene isomers of approximately 0.25). In comparison, the Mixed Xylenes distillation cut from an STDP unit or a selective toluene alkylation unit can have a paraxylene to total xylene isomer ratio of greater than 0.7, more typically above 0.8, and often above 0.9.

Thus, a paraxylene producer may purchase Mixed Xylenes as feed to a paraxylene unit, or they may purchase or produce other sources of xylene isomers, all having widely different proportions of paraxylene therein. Where the proportion of paraxylene in the Mixed Xylenes is relatively low, a first paraxylene separation stage may be carried out and the remaining paraxylene-depleted stream may be further processed to produce additional paraxylene. Such a process may be carried out in a paraxylene unit, which is typically comprised of three sections: a paraxylene recovery section, an isomerization section, and a fractionation section. The purpose of the paraxylene recovery section is to generate a paraxylene product stream and a paraxylene lean stream, known as reject or raffinate. The paraxylene lean stream is directed to the isomerization section that comprises a reactor and a catalyst used to isomerise the xylenes in the reject stream to a near equilibrium distribution. The catalyst should also convert any ethylbenzene present in the mixture to either xylenes or by-products that can readily be separated in the fractionation section, to prevent its build up in a recycle loop generated within the paraxylene unit. Any non-aromatics present should also be converted, typically by cracking to smaller hydrocarbons to prevent their build up.

Xylene isomerization catalysts are typically categorized by the way they convert ethylbenzene. For example, ethylbenzene isomerization-type catalysts (also known as naphthene pool catalysts) have the ability to convert a portion of the ethylbenzene to xylene isomers via C8 naphthene intermediates. Ethylbenzene dealkylation-type catalysts convert ethylbenzene primarily via reaction with hydrogen to form benzene and ethane. Ethylbenzene transalkylation-type catalysts convert ethylbenzene primarily by the transfer of the ethyl group to another ethyl benzene or to a xylene. All of these catalysts produce by-products from the ethylbenzene conversion reactions and/or side reactions that must be separated in the fractionation section. These by-products include benzene, toluene, and C9-plus aromatics. Benzene is a valuable by-product, and is generally recovered in high purity by additional fractionation equipment or by extraction or extractive distillation.

Two popular methods for recovering paraxylene in the paraxylene recovery section are crystallization and selective adsorption. Selective adsorption processes include the UOP Parex process described in R A Meyers (editor) Handbook of Petroleum Refining Processes, Third Edition (2004) and the Axens Eluxyl process described in G Ash, et al, Oil and Gas Technology, 49 (5), 541-549 (2004).

Paraxylene crystallization recovery sections generally contain several stages in order to achieve final product purity and to improve efficiency. Examples include a two stage paraxylene crystallization recovery section comprising two crystallization stages, a three stage paraxylene crystallization recovery section comprising three crystallization stages, a single reslurry paraxylene crystallization recovery section comprising two crystallization stages and one reslurry stage, and a double reslurry paraxylene crystallization recovery section comprising one crystallization stage and two reslurry stages.

In one known process, a single temperature crystallization product stage is used for producing paraxylene from a feed having an above equilibrium paraxylene concentration, such as from a toluene disproportionation process. Scavenger stages are also used to raise the paraxylene recovery rate. The process uses a single temperature production stage comprising one or more crystallizer vessels in parallel, i.e. the paraxylene-rich stream is fed to the crystallization stage and not to a reslurry stage.

A further known process uses crystallization technology to purify paraxylene simultaneously of large concentrations of C8 aromatics and also small concentrations of oxygenated species. This process comprises a first stage in which a paraxylene feed is cooled, crystallized and separated at a very cold temperature for maximum recovery, following which the crystals are melted and recrystallized and separated at a warmer temperature.

U.S. Pat. No. 6,565,653 relates to a process to produce high purity paraxylene from a feed comprising at least 55 to 60 wt % paraxylene, wherein a first portion of the high purity paraxylene is obtained in a first crystallization step at about 10° F. to about 55° F. without the need for further reslurry and crystallization, and wherein another portion of the high purity paraxylene product is obtained following a reslurry step, which warms crystalline paraxylene obtained from subsequent lower temperature crystallizations to yield a slurry at a temperature of about 10° F. to about 55° F., without the need for further refrigeration. The disclosed process includes crystallization stages and reslurry stages, but the first step of the process is crystallizing the paraxylene-rich feedstream in a first crystallizer.

U.S. Pat. No. 7,405,340 relates to a process for recovering paraxylene that comprises cooling the hydrocarbon feedstock in at least one refrigerated crystallization stage that is indirectly refrigerated by evaporating at least a portion of a substantially liquid stream comprising ammonia. The process is said to be carried out using a crystallization paraxylene recovery section for recovering paraxylene from paraxylene-rich STDP xylenes with each stage comprised of crystallizers, and where heat can be removed from the crystallizers via indirect contact with an ammonia refrigerant. The ammonia refrigeration cycle is an ammonia absorption refrigeration cycle.

U.S. Pat. No. 2010/0041936 relates to a process for separating solids from a solid-liquid slurry, such as paraxylene from a Mixed Xylene slurry, incorporating a crystallization stage and one or more reslurry stages. In a particular embodiment, the process is said to include two reslurry stages, and the ratio of paraxylene to total xylene isomer, in the product of each stage is said to generally increase throughout the process.

In separating paraxylene from a C8 aromatic hydrocarbon feed, crystallization is often preferred over adsorption and distillation because crystallization does not require a costly adsorbent (as in adsorption processes), and because xylene isomers and ethylbenzene have undesirably similar boiling points (making distillation difficult) but dramatically different melting points. Pure paraxylene freezes at 56° F. (13° C.), pure metaxylene freezes at −54° F. (−48° C.), pure orthoxylene freezes at −13° F. (−25° C.) and pure ethylbenzene freezes at −139° F. (−95° C.). Where paraxylene is present in such mixed feedstreams in low concentrations, very low temperatures are generally required to effectively recover the paraxylene from the feedstreams by crystallization.

There remains a need to find processes that seek to optimize the recovery of paraxylene from mixed feedstreams thereof.

SUMMARY

In one aspect of the invention, a process is provided for recovering paraxylene from at least two feedstreams containing xylene isomers, comprising:
directing to a paraxylene recovery zone a paraxylene-lean feedstream having a paraxylene to total xylene isomer ratio of 0.50 or less, the paraxylene recovery zone comprising at least one crystallization zone;
directing to the paraxylene recovery zone a paraxylene-rich feedstream having a paraxylene to total xylene isomer ratio of greater than 0.50; and
recovering from the paraxylene recovery zone a paraxylene containing product stream having a paraxylene to total xylene isomer ratio greater than that of the pX-rich feedstream.

In an example of the invention the paraxylene-rich feedstream comprises at least a portion of an effluent downstream of a second paraxylene recovery zone, for example a paraxylene recovery zone comprising at least one crystallization zone and/or at least one reslurry zone. The use of the paraxylene-rich feedstream from the second paraxylene recovery zone as a feedstream in the first paraxylene recovery zone improves the efficiency and/or cost effectiveness of at least the first paraxylene recovery zone, and preferably the overall efficiency and/or cost effectiveness of both paraxylene recovery zones.

The foregoing aspects are illustrative of those that can be achieved by the present invention and are not intended to be exhaustive or limiting of the possible advantages which can be realised. Thus, these and other aspects of the invention will be apparent from the description herein or can be learned from practicing the invention, both as embodied herein or as modified in view of any variation which may be apparent to those skilled in the art.

BRIEF DESCRIPTION OF THE DRAWINGS

For a more complete understanding of the disclosure, reference should be made to the following detailed description and accompanying drawings wherein.

Figure 1:
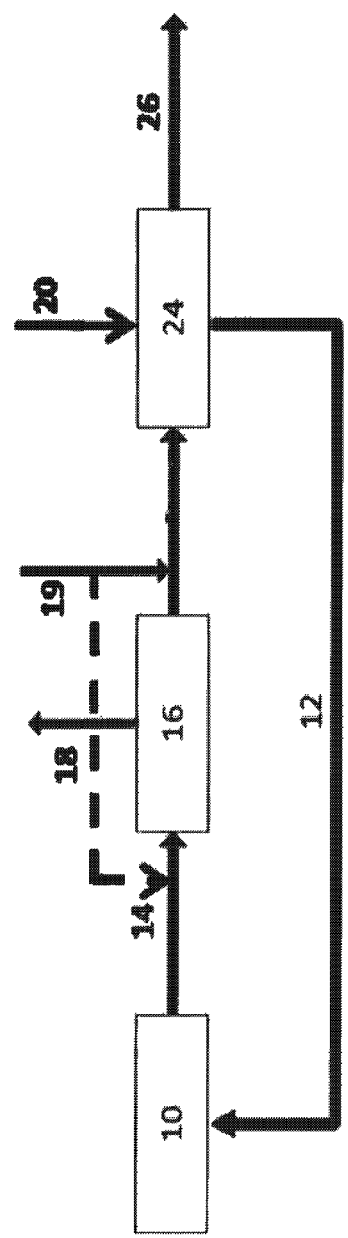
FIG. 1 is a flow diagram illustrating an embodiment of a method for paraxylene recovery.

While the disclosed processes are susceptible of embodiments in various forms, specific embodiments of the invention are illustrated in the drawings (and will hereafter be described) with the understanding that the disclosure is intended to be illustrative, and is not intended to limit the invention to the specific embodiments described and illustrated herein.

DETAILED DESCRIPTION OF THE PREFERRED EMBODIMENTS

A method according to one embodiment of the present invention is directed to a process for recovering paraxylene from at least two feedstreams containing xylene isomers. The process comprises directing to a paraxylene recovery zone a paraxylene-lean feedstream having a paraxylene to total xylene isomer ratio of 0.50 or less, the paraxylene recovery zone comprising at least one crystallization zone. The process also comprises directing to the paraxylene recovery zone a paraxylene-rich feedstream having a paraxylene to total xylene isomer ratio of greater than 0.50. The process further comprises recovering from the paraxylene recovery zone a paraxylene containing product stream having a paraxylene to total xylene isomer ratio greater than that of the paraxylene-rich feedstream.

As used herein the term "paraxylene to total xylene isomer ratio" means the weight of paraxylene divided by the total weight of all isomers of xylene (i.e. paraxylene, metaxylene and orthoxylene) expressed as a fraction.

As used herein, the term "effluent downstream of" a particular source means an effluent derived directly or indirectly from that source. Thus, for example, an effluent downstream of a non-selective toluene disproportionation unit refers to an effluent that originated in such a unit but which may have been subsequently processed in one or more other units. Specifically, a stream produced in an isomerization zone and subsequently processed in a fractionation zone may be referred to as an effluent downstream of an isomerization zone.

The paraxylene recovery zone to which the two feedstreams are directed (sometimes referred to hereafter as the first recovery zone) has at least one crystallization zone and, in a particular embodiment, at least a portion (and optionally all) of the paraxylene-lean feedstream is directed to the at least one crystallization zone.

The crystallization zone is a zone in which liquid paraxylene is crystallized from a feedstream comprising paraxylene and additional components, for example including metaxylene, orthoxylene and/or ethylbenzene. The paraxylene is generally caused to crystallize by cooling the feedstream to a temperature below the freezing point of the paraxylene but preferably above the freezing point of the other components in the feedstream. More particularly, the temperature is selected to seek to optimize the crystallization of paraxylene, for example by selecting a temperature at which paraxylene freezes but which is above the eutectic temperature (the eutectic temperature is the temperature at which a xylene isomer other than paraxylene begins to co-crystallize). The paraxylene-metaxylene and paraxylene-orthoxylene eutectic temperatures can be close depending on the composition within the crystallizer, so either metaxylene or orthoxylene may be the first isomer to begin to co-crystallize. For non-selective feedstocks, the eutectic temperature is typically around −88° F. (−67° C.) to around −94° F. (−70° C.).

The crystallization zone may comprise a single crystallization vessel (crystallizer) or multiple crystallization vessels may be used in series, with each subsequent crystallization vessel being cooled to a lower temperature.

The low temperatures required to crystallize paraxylene from xylene mixture are typically achieved by a cascaded vapour compression refrigerant system using a Deep Refrigerant. A Deep Refrigerant is defined as one for which it is generally not possible, or not economic, to compress its vapour or gas to a pressure level where it can be condensed by air or water cooling. Ethylene is a Deep Refrigerant, because its critical temperature is 49° F. (9.5° C.), and its critical pressure is 50.76 bar. Thus, for most places on earth, for at least part of the year, ethylene is a gas above its critical temperature at ambient temperature, and it is not possible to condense ethylene via air or water cooling. When used as a refrigerant, ethylene is usually condensed by transferring heat to a High Level Refrigerant. A High Level Refrigerant is defined as one for which it is possible to condense its vapour against air or water. Thus, a cascaded ethylene/propylene, ethylene/propane, or ethylene/ammonia refrigeration system can be used to achieve the low temperatures required for paraxylene crystallization.

Effluent from the crystallization zone typically contains around 18 wt % paraxylene solids, and it will typically therefore be necessary to separate these solids in one or more solid-liquid separation devices. Suitable separation devices may include filter columns, wash columns, centrifuges or any other types of solid-liquid separators known in the art.

A filter column is a solid-liquid separation apparatus for concentrating a suspension. Examples of suitable filter columns are disclosed in US patent application publication Nos. 2005/0056599 and 2007/0225539, the disclosures of which are hereby incorporated herein by reference. A suitable filter column includes a hollow cylinder containing one or more tubes having a specified outer diameter and extending in an axial direction within the hollow cylinder. The wall of each tube includes at least one filter that forms the only direct connection between the interior of the tube and the interior of the hollow cylinder. The filter column separates solids from liquids in a solid-liquid suspension (e.g. a solid product component suspended in a mother liquid) by directing the suspension into a first end of the filter column. A displacement fluid (e.g. a gas or liquid immiscible with the suspension liquid) applies a back-pressure to the second end of the filter column, helping to drive a portion of the suspension liquid through the filter into the tube interior to be withdrawn as a filtrate (e.g. a mother liquid) from the filter column tubes, thereby forming a concentrated suspension (i.e. bed) of solids in the hollow cylinder and around the tubes. The concentrated suspension of solids is withdrawn from the second end of the filter column via a product overflow chute, for example in the form of concentrated product containing small amounts of suspension liquid (e.g. mother liquid) and/or displacement fluid.

A wash column (or a hydraulic wash column) is a solid-liquid separation apparatus for concentrating a suspension. A wash column separates solids from liquids in a solid-liquid suspension (e.g. a solid product component suspended in a mother liquid) by directing the suspension into a first end of a wash column and a wash liquid into a second end of the wash column in countercurrent flow to the suspension, thereby forming a bed of the solids. The wash liquid introduced into the wash column reslurries the bed and can melt some of the recovered solids.

Centrifuges that are suitable for use as solid-liquid separators are not particularly limited and include those generally known in the art, such as, for example, filtering centrifuges, and in particular screen-bowl, solid-bowl, and/or pusher centrifuges. A suitable centrifuge generally includes an inlet for a solid-liquid suspension (e.g. a solid product component suspended in a mother liquor) to be separated, a first outlet for the concentrated solid suspension (e.g. product filter cake), and a second outlet for the filtered liquid (e.g. mother liquor) from the inlet suspension. In some embodiments (e.g. when a screen bowl centrifuge is used), the centrifuge includes a third outlet for filtered liquid from the inlet suspension, with the second and third outlet streams differing in the relative amounts of solids (e.g. residual, unrecovered product component) contained in each. In such embodiments, the second outlet can be a low solids filtrate streams and the third outlet can be a high-solids filtrate stream.

Separation of the effluent from the crystallization zone produces a filtrate and a relatively paraxylene-rich cake. Eutectic formation limits paraxylene recovery in the crystallization zone, and thus the filtrate contains at least some paraxylene. Alternatively or additionally at least a portion of the filtrate may be sent to an isomerization section to produce further paraxylene and/or remove ethylbenzene and any non-aromatics from the process.

The cake obtained by separating the effluent from the crystallization stage contains paraxylene crystals with adhered mother liquor that contains ethylbenzene, other xylene isomers, unrecovered paraxylene and other components of the feedstream. Preferably therefore, the cake is further processed to improve the purity of the paraxylene content.

In a particular embodiment, the paraxylene recovery zone further comprises at least one reslurry zone.

A reslurry zone incorporates one or more reslurry drums in which an upstream filter cake of product component crystals is equilibrated with a usually warmer diluent stream comprising an additional (liquid) product component to provide a slurry suitable for downstream processing. Suitable reslurry drums and reslurry zones are disclosed in U.S. Pat. No. 6,565,653 and US Patent Application No. US 2012/0178980, the disclosures of which are hereby incorporated herein by reference. A solid cake of product component crystals and a liquid diluent containing both liquid product and secondary components are fed to an inlet of a suitable reslurry drum. The solid cake and liquid diluent can be added to the reslurry drum separately (i.e. via two different feed lines), or they can be mixed upstream of the reslurry drum and added thereto via a single feed line. The reslurry drum is a reservoir containing product component crystals, and has sufficient volume/residence time to equilibrate the product component crystals with the liquid product component in the reservoir. The reslurry drum contents are preferably agitated while equilibrating. A slurry (i.e. solid-liquid suspension) effluent exits the reslurry drum through an outlet. The slurry effluent has product components crystals dispersed in a liquid including the liquid secondary component and a portion of the non-crystallized liquid product component.

The paraxylene-lean feedstream having a paraxylene to total xylene isomer ratio of less than 0.50 may be obtained from any suitable source. In a particular embodiment the paraxylene-lean feedstream comprises at least a portion of an effluent downstream of a non-selective source of Mixed Xylenes. Such non-selective sources of Mixed Xylenes may include a refinery catalytic reformer, a non-selective toluene disproportionation unit, a non-selective toluene/aromatic C9-plus transalkylation unit, a non-selective aromatic C9-plus transalkylation unit and a non-selective toluene methylation unit.

The paraxylene-lean feedstream may be derived directly from the non-selective source of Mixed Xylenes or it may have been further processed before being used in the process of the present invention, for example to alter the proportion of xylene isomers and/or other components therein. Thus, in a particular embodiment, the paraxylene-lean feedstream comprises at least a portion of an effluent downstream of an isomerization zone. Furthermore, the paraxylene-lean feedstream may comprise at least a portion of an effluent downstream of a fractionation zone.

Generally, the paraxylene-rich feedstream having a paraxylene to total xylene isomer ratio of greater than 0.50 may be derived from any suitable source capable of producing mixtures comprising high proportions of paraxylene. Suitable sources include a selective toluene disproportionation (STDP) unit and a selective toluene alkylation unit. In another embodiment, the paraxylene-rich feedstream may comprise at least a portion of an effluent downstream of a second paraxylene recovery zone. The second paraxylene recovery zone may be any conventional paraxylene recovery zone known in the art, but in a preferred embodiment the second paraxylene recovery zone comprises at least one crystallization zone comprising at least one crystallizer. The crystallization zone of the second paraxylene recovery zone may be any suitable crystallization zone, but is preferably a single or multistep crystallization zone, as disclosed herein with respect to the first paraxylene recovery zone.

The at least one crystallizer of the second paraxylene recovery zone may be cooled in any manner, but preferably it is cooled by a high level refrigerant, such as propylene, propane or ammonia.

Alternatively or additionally, the second paraxylene recovery zone may comprise at least one reslurry zone. The reslurry zone of the second paraxylene recovery zone may be any suitable reslurry zone known in the art, but preferably comprises a reslurry drum, as discussed herein with respect to the first paraxylene recovery zone.

Alternatively or additionally, the second recovery zone may comprise at least one selective adsorption zone, such as any conventionally known paraxylene adsorption zone.

A selective adsorption zone contains an adsorbent which is either more selective for metaxylene and orthoxylene, or more selective for paraxylene, from the feedstream. In either case, two streams are produced, the first being a paraxylene depleted stream and the second being a paraxylene enriched stream.

Where the paraxylene-rich feedstream comprises at least a portion of an effluent downstream of a second paraxylene recovery zone, any proportion of the effluent of the second paraxylene recovery zone may be directed to the first paraxylene recovery zone. Preferably, the proportion of the effluent of the second paraxylene recovery zone directed to the first paraxylene recovery zone is chosen as to improve the production rate and/or overall cost effectiveness of at least the first paraxylene recovery zone. For example, the paraxylene recovery rate of the first paraxylene recovery zone may be increased by 5% or more up to 50% or more, for example by 10% or by 38%. Cost effectiveness may also be improved by, for example, modifying the heating or cooling requirements in the first paraxylene recovery zone, for example by reducing heating of one or more of the recycle streams to one or more of the reslurry stages. Most preferably the overall paraxylene production efficiency and/or cost effectiveness of the combined paraxylene recovery zones is improved.

In one embodiment, the paraxylene-lean feedstream preferably has a ratio of paraxylene to total xylene isomers of 0.4 or less. Alternatively, or additionally, the paraxylene-lean feedstream preferably has a ratio of paraxylene to total xylene isomers of 0.15 or more.

In one embodiment, the paraxylene-rich feedstream has a ratio of paraxylene to total xylene isomers of 0.55 or more, preferably 0.70 or more, even more preferably 0.80 or more, and even more preferably 0.90 or more.

In a particular embodiment, the paraxylene containing product stream has a concentration of paraxylene of at least 99.0 wt %, preferably at least 99.5 wt %, and more preferably at least 99.7 wt %.

In a particular embodiment, at least a portion of the paraxylene-rich feedstream is directed to the at least one reslurry zone of the first paraxylene recovery zone. This may be additional to any product of the crystallization zone of the first paraxylene recovery zone that may be also be directed to the reslurry zone of the first paraxylene recovery zone.

Where two feeds are directed to the reslurry zone, they may be fed separately or mixed before entry into the reslurry zone.

In a particular embodiment in which the paraxylene recovery zone comprises at least one reslurry zone, the at least one reslurry zone may comprise at least one efficiency stage and a product stage downstream of the at least one efficiency stage, and at least a portion of the paraxylene-rich feedstream is directed to the product stage. An "efficiency stage" is a first reslurry stage, which generally produces an intermediate stage product, and a "product stage" is a subsequent reslurry stage, which generally produces a final product. The paraxylene-rich feedstream directed to the product stage may be additional to any other paraxylene containing stream directed to the product stage, such as a stream derived directly or indirectly from the crystallization stage or the efficiency stage of the first paraxylene recovery zone. Where two or more feedstreams are directed to the product stage, they may each be fed directly to the product stage or they may be combined before being fed to the product stage.

Preferably, at least a portion of the paraxylene-rich feedstream is cooled prior to its introduction to the product stage. Alternatively, at least a portion of the paraxylene-rich feedstream may be warmed prior to its introduction to the product stage. In some embodiments however, no temperature adjustment is required.

The efficiency stage of the reslurry zone of the first paraxylene recovery zone typically comprises one or more slurry drums in which a paraxylene cake, for example obtained by a solid-liquid separation of the product of the crystallization zone, is reslurried, for example with reject filtrate from the efficiency stage. The temperature of the efficiency stage reslurry drum is typically about 25° F. (−10° C.) to about 0° F. (−18° C.).

The solids content of the effluent from the efficiency stage reslurry drums is typically controlled to around 40 wt % to around 50 wt %. This stream may therefore be sent to a solid/liquid separation device, such as, for example, a filter column, a wash column or a centrifuge. Any suitable solid/liquid separation device may be used, as discussed herein with respect to separation of the effluent from the crystallization stage. The liquid effluent obtained from the solid/liquid separation device may be removed from the system, but preferably at least a portion is recycled to the efficiency stage reslurry drum and/or or at least a portion is recycled to the crystallization zone. The solid effluent obtained from the solid/liquid separation device comprises paraxylene, and generally has a higher paraxylene concentration than the concentration in the feed to the slurry zone; however, the paraxylene concentration may be increased further by reslurrying, for example in a product stage. The solid effluent may contained adhered liquid comprising the other pX isomers and other impurities contained in the feed to the solid/liquid separation devices.

The product stage of the first paraxylene recovery zone preferably comprises one or more slurry drums in which the solid effluent from the efficiency stage is reslurried, preferably with liquid recycle streams from the product stage. Any suitable reslurry drum may be used, and the product stage is generally operated at temperatures of about 39° F. (−4° C.) to about 44° F. (7° C.).

The effluent from the product stage reslurry drum may be further processed in a solid/liquid separation device such as a filer column, wash column or centrifuge. Any suitable solid/liquid separation device may be used, for example a device as discussed herein with respect to the efficiency stage or the crystallization zone. Liquid is extracted from the product stage effluent in the separation device, and may be removed from the system, but preferably at least a portion is recycled to the product stage slurry drum and/or at least a portion is recycled to the efficiency stage slurry drum.

The solid component of the effluent of the product stage slurry drum obtained in the solid/liquid separation device may be melted to form paraxylene containing product stream having a paraxylene to total xylene isomer ratio greater than that of the paraxylene-rich feedstream; however, at least a portion of the melted solid component may be recycled to the solid/liquid separation device.

In at least one embodiment, at least a portion of the paraxylene-rich feedstream is cooled, preferably before being directed to the paraxylene recovery zone, by a high level refrigerant. Any high level refrigerant is suitable, such as propylene, propane and ammonia.

In another embodiment, at least a portion of the paraxylene-rich feedstream is cooled, preferably before being directed to the paraxylene recovery zone, by chilled water or a chilled glycol solution.

In a particular embodiment, at least a portion of the paraxylene-rich feedstream may be directed to the at least one crystallization zone of the first paraxylene recovery zone. This may be an alternative to, or additional to, the directing of at least a portion of the paraxylene-rich feedstream to any other section of the first paraxylene recovery zone, such as the reslurry zone.

Advantageously, the at least one crystallization zone of the first paraxylene recovery zone comprises at least two stages in series, and the paraxylene-rich feedstream is directed to a stage other than the first stage. For example, the crystallization zone may comprise three crystallization stages, and the paraxylene-rich feedstream may be directed to the second or the third stage.

Preferably, where at least a portion of the paraxylene-rich feedstream is directed to the at least one crystallization zone, it is cooled prior to its introduction thereto with a high level refrigerant. Any suitable high level refrigerant may be used, including propylene, propane and ammonia.

Alternatively, where at least a portion of the paraxylene-rich feedstream is directed to the at least one crystallization zone, it may be cooled prior to its introduction thereto with an indirect cooling medium. Any suitable indirect cooling medium may be used, for example chilled water or a chilled glycol solution.

In the embodiment illustrated in FIG. 1, an isomerization unit 10 receives a hydrocarbon-containing feedstream 12. The hydrocarbon containing feedstream 12 comprises xylene isomers (preferably at least 80 wt %) and may also comprise ethylbenzene, but has a very low paraxylene content (generally less than 12 wt % paraxylene with respect to the total xylenes). In the isomerization unit 10, the hydrocarbon-containing feedstream 12 is contacted with an isomerization catalyst under conditions suitable to yield a first paraxylene feedstream 14. The first paraxylene feedstream 14 is a paraxylene-lean feedstream, i.e. although it is enriched in paraxylene with respect to the hydrocarbon-containing feedstream 12 it has a paraxylene to total xylene isomer ratio of 0.50 or less, generally 0.4 or less. Optionally, the first paraxylene feedstream 14 may be further processed 16 to recover by-products 18 from the first paraxylene feedstream 14. Typical by-products 18 include, but are not limited to benzene, toluene, trimethylbenzene, methyl(ethyl)benzene, and the like, which may be isolated from the first paraxylene feedstream 14 by standard methods, such as fractional distillation. In certain embodiments, the first paraxylene feedstream 14 is processed 16 to recover benzene by-products and/or toluene by-products. The effluent exiting processing zone 16 is introduced to a paraxylene recovery zone 24. A second paraxylene feedstream 19 may be also introduced to paraxylene recovery zone 24. The second paraxylene feedstream 19 is also paraxylene-lean, and has a paraxylene content such that the combined paraxylene to total xylene isomer ratio of the first and second paraxylene feedstreams 14 and 19 is 0.50 or less. The second paraxylene feedstream 19 can be obtained from any non-selective source of Mixed Xylenes, such as a refinery catalytic reformer, a non-selective toluene disproportionation unit, a non-selective toluene/aromatic C9-plus transalkylation unit, a non-selective aromatic C9-plus transalkylation unit and a non-selective toluene methylation unit. The second paraxylene feedstream 19 may also comprise a downstream effluent from a fractionation zone.

Where processing 16 of the first paraxylene feedstream 14 is carried out, the first and second paraxylene feedstreams 14 and 19 may be combined either before or after the processing 16. Where the first and second paraxylene feedstreams 14 and 19 are combined before the processing 16, this allows the recovery not only of by-products produced in the isomerization zone 10, but also a portion of any non-C8 aromatic components present in second paraxylene feedstream 19. For example, where second paraxylene feedstream 19 is a C8-plus distillation cut from a reformer, processing 16 allows the removal not only of by-products produced in the isomerization zone 10, but also C9-plus components present in the C8-plus reformate stream.

A third paraxylene feedstream 20 is also introduced to the paraxylene recovery zone 24.

The third paraxylene feedstream 20 is a paraxylene-rich feedstream having a paraxylene to total xylene isomer ratio of greater than 0.50. The third paraxylene feedstream 20 may be obtained from any suitable source, including a feedstream downstream of an STDP unit, a selective toluene alkylation unit or a second paraxylene recovery zone.

Paraxylene recovery zone 24 which comprises at least one crystallization zone. In the paraxylene recovery zone 24, a paraxylene product stream 26 is formed having a paraxylene to total xylene isomer ratio greater than the second paraxylene feedstream and a hydrocarbon-containing feedstream 12 having a paraxylene to total xylene isomer ratio less than that of the first paraxylene feedstream 14.

Figure 2:
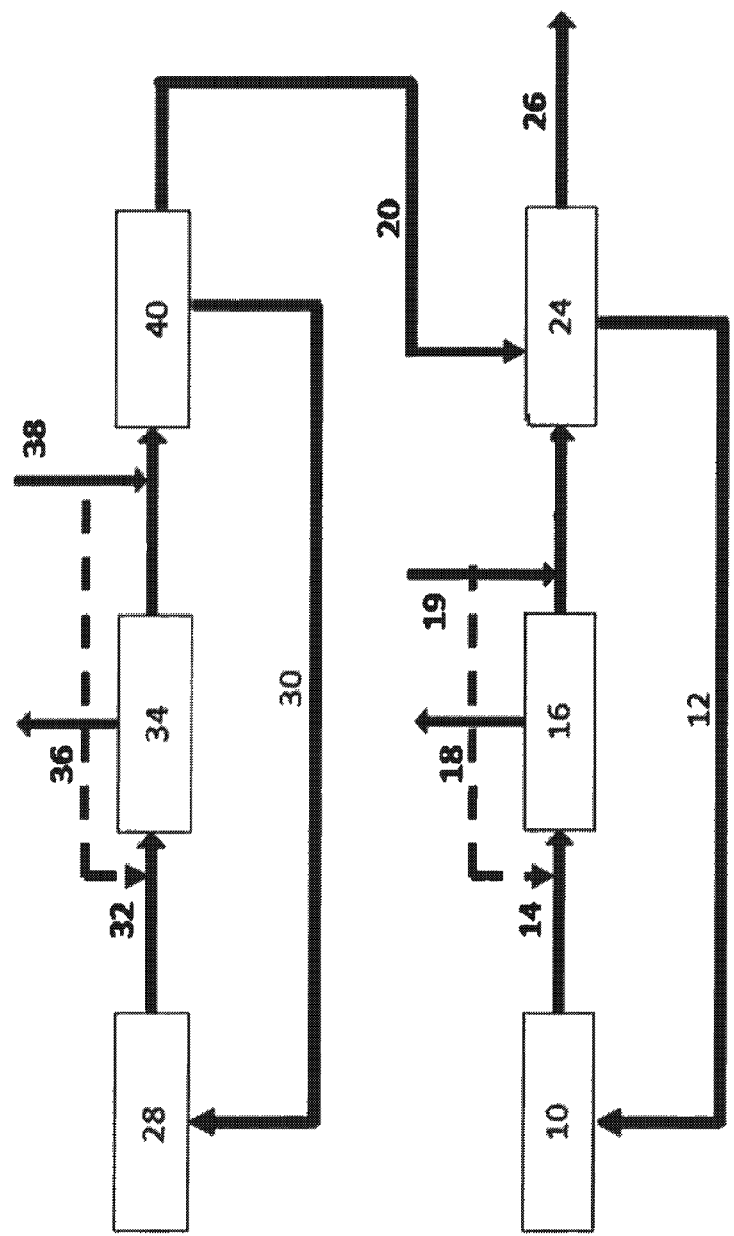
FIG. 2 is a flow diagram illustrating another embodiment of a method for paraxylene recovery.

In the embodiment illustrated in FIG. 2, two paraxylene recovery zones are integrated to provide improved efficiency and/or cost effectiveness. The first paraxylene recovery zone 24 operates as discussed in the embodiment illustrated in FIG. 1, but, as shown in FIG. 2, the third paraxylene feedstream 20 is obtained from a second paraxylene recovery zone 40.

The second paraxylene recovery zone 40 may be any conventional paraxylene recovery zone. For example, the second paraxylene recovery zone 40 may comprise one or more components including crystallization units, reslurry units, and/or adsorption units. The second paraxylene recovery zone 40 is supplied with a fourth paraxylene feedstream 32 and a fifth paraxylene feedstream 38. The fourth paraxylene feedstream 32 is produced in a second isomerization unit 28. The second isomerization unit 28 receives a second hydrocarbon-containing feedstream 30 which comprises at least 80 wt % xylene isomers, but has a paraxylene to total xylene isomer ratio of 0.12 or less. In the second isomerization reactor 28, the second hydrocarbon containing feedstream 30 is contacted with an isomerization catalyst under conditions suitable to yield the fourth paraxylene feedstream 32. The fourth paraxylene feedstream 32 is a paraxylene-lean feedstream having a paraxylene to total xylene isomer ratio of 0.50 or less, but a paraxylene to total xylene isomer ratio greater than that of the second hydrocarbon-containing feedstream 30. Optionally, the third paraxylene feedstream 32 may be further processed 34 to recover by-products 36 from the third paraxylene feedstream 32. Typical by-products 36 include, but are not limited to, the by-products 18 referred to with respect to the first paraxylene feedstream 14.

The fifth paraxylene feedstream 38 may comprise any source of paraxylene, but is generally a paraxylene-lean feedstream, having a paraxylene content such that the paraxylene to total xylene ratio of the fourth and fifth paraxylene feedstreams 32 and 38 is 0.50 or less. The fifth paraxylene feedstream 38 can be obtained from any non-selective source of Mixed Xylenes, such as a refinery catalytic reformer, a non-selective toluene disproportionation unit, a non-selective toluene/aromatic C9-plus transalkylation unit, a non-selective aromatic C9-plus transalkylation unit and a non-selective toluene methylation unit. The fifth paraxylene feedstream 38 may also comprise a downstream effluent from a fractionation zone. As discussed with respect to the embodiment shown in FIG. 1, the fourth and fifth paraxylene feedstreams 32 and 38 may be mixed before or after the optional further processing step 34.

The fourth and fifth paraxylene feedstreams 32 and 38 are directed to the second separation unit 40, either separately or in combination, where they are separated to form the third paraxylene feedstream 20 and the second hydrocarbon-containing feedstream 30. The third paraxylene feedstream 20 is a paraxylene-rich feedstream having a paraxylene to total xylene isomer ratio of greater than 0.50, and directed to the first paraxylene recovery zone 24. The second hydrocarbon-containing feedstream 30 is recycled to the second isomerization unit 28 to produce further paraxylene.

The methods illustrated in FIGS. 1 and 2 may be carried out as batch, semi-continuous or continuous operations.

Figure 3:
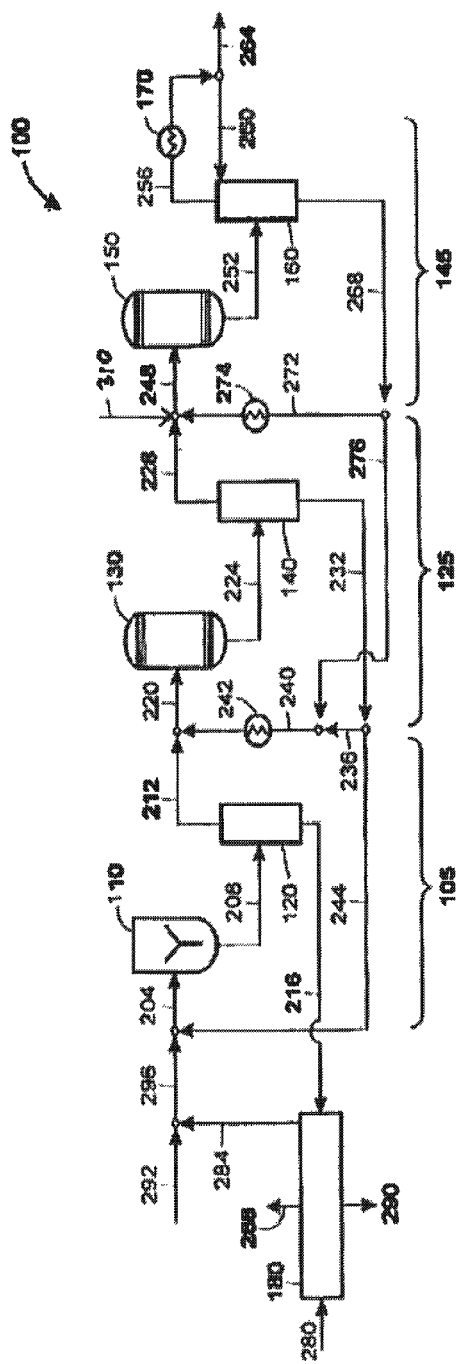
FIG. 3 is a process flow diagram illustrating an embodiment of a crystallization/reslurry process wherein a paraxylene-lean feedstream and a paraxylene-rich feedstream are processed in a paraxylene recovery zone.

FIG. 3 illustrates a crystallization/reslurry process 100 using a crystallization stage 105, followed by a first reslurry stage 125 and a second reslurry stage 145 in connection with at least one solid/liquid separator to recover a solid (crystalline) paraxylene containing product stream from at least two feedstreams containing xylene isomers, which solid product component can be subsequently melted to form a substantially pure liquid paraxylene stream. One of the two feedstreams containing xylene isomers has a paraxylene to total xylene isomer ratio of 0.50 or less, and the other of the feedstreams has a paraxylene to total xylene isomer ratio of greater than 0.50, whilst the paraxylene containing product stream has a paraxylene to total xylene isomer ratio greater than that of the paraxylene-rich feedstream. The crystallization stage 105 includes a crystallizer 110 and a separation unit 120. The crystallization stage 105 is followed by a first ("efficiency") reslurry stage 125, which includes a reslurry drum 130 and a separation unit 140. The first reslurry stage 125 is followed by the second (or "product" or "final") reslurry stage 145, which includes a reslurry drum 150 and a separation unit 160.

In the embodiment illustrated in FIG. 3 the paraxylene purification recovery process begins by feeding a liquid paraxylene-lean feedstream 296 having a paraxylene to total xylene isomer ratio of 0.50 or less to the crystallizer 110. The feedstream 204 includes liquid paraxylene, together with other xylene isomers (i.e. orthoxylene and metaxylene), and ethylbenzene (together herein referred to as the "liquid secondary component"), and possibly other components (such as non-aromatic compounds with boiling points close to the xylenes, toluene and aromatic C9-plus compounds). The precise composition of the paraxylene-lean feedstream 204 will depend upon its source, which can include any non-selective source of Mixed Xylenes, such as a refinery catalytic reformer, a non-selective toluene disproportionation unit, a non-selective toluene/aromatic C9-plus transalkylation unit and a non-selective aromatic C9-plus transalkylation unit. The paraxylene-lean feedstream 204 may also comprise at least a portion of an effluent downstream of an isomerization zone 180 and/or a downstream effluent from a fractionation zone (not shown).

The crystallizer 110 operates at a temperature sufficient to crystallize at least a portion of the paraxylene from the paraxylene-lean feedstream 204 to form a slurry effluent 208, which includes both paraxylene crystals and liquids secondary component of the feedstream. For example, when the feedstream 204 includes about 22 wt % paraxylene, a suitable crystallization temperature and atmospheric pressure is about −89° F. (−67° C.), or about 2° F. (1.1° C.) warmer than the binary eutectic temperature of about −91° F. (−68° C.). In a continuous paraxylene purification process, the residence time in the crystallizer 110 preferably is sufficient to crystallize a substantial portion of the paraxylene component in the feedstream 204, for example at least about 50 wt % (more preferably at least about 70 wt %) of the liquid product component in the feedstream 204.

The slurry effluent 208 is then fed to the separation unit 120, which may be a filter column, a wash column or a centrifuge. The separation unit 120 at least partially separates the paraxylene crystals and the liquid secondary component of the slurry effluent 208 to form a filter cake 212 and a filtrate 216. The filter cake 212 is predominantly a solid cake of paraxylene crystals. Preferably, substantially all of the paraxylene crystals from the slurry effluent 208 are recovered in a filter cake 212, and the filter cake 212 has a total paraxylene weight concentration (i.e. liquid and solids combined) greater than that of the filtrate 216. The filter cake 212 also includes a small amount of liquid, generally including both the liquid secondary component and liquid paraxylene. Specifically, the filter cake 212 preferably includes about 50 wt % to about 99 wt % (more preferably about 75 wt % to about 88 wt %) paraxylene crystals, based on the total weight of the filter cake, including any liquids. The filtrate 216 is predominantly a liquid stream of the liquid secondary component, and preferably substantially all of the liquid secondary component from the slurry effluent is recovered in the filtrate 216. However, the filtrate 216 can include a small amount of liquid paraxylene and/or paraxylene crystals. In general, the filtrate 216 can either be discarded as a reject stream or, preferably, recycled for further processing.

The filter cake 212 and a reslurry diluent 240 are then fed to the first reslurry drum 130 via a stream 220. The reslurry diluent 240 is a liquid stream including both the liquid paraxylene and the liquid secondary component. As illustrated in FIG. 3, the filter cake 212 and the reslurry diluent 240 are mixed upstream of the first reslurry drum 130 and then fed thereto via the single stream 220. In an alternative embodiment (not shown) however, the filter cake 212 and the reslurry diluent 240 can be fed to the first reslurry drum 130 as two separate streams.

The first reslurry drum 130 is a reservoir containing a solid-liquid slurry including paraxylene crystals, liquid paraxylene and the liquid secondary component. In the slurry drum 130, the paraxylene crystals are equilibrated with the liquid paraxylene and the liquid secondary component for a time sufficient to form a reslurry effluent 224. The equilibrium warms the reslurry effluent relative to the temperature of the filter cake 212. In a continuous process, the volume of the reslurry drum 130 and the feed rates of the filter cake 212 and the reslurry diluent 240 can be selected to provide a sufficient residence time for equilibration.

The reslurry effluent 224 is then fed to the separation unit 140, which operates analogously to the separation unit 120. The separation unit 140 can be a filter column, wash column or centrifuge. The separation unit 140 forms a filter cake 228 and a filtrate 232. While the filtrate 232 can be discarded as a reject stream, it is preferably recycled for further processing. As illustrated in FIG. 3, a portion 236 of the filtrate 232 is recycled to the first reslurry drum 130 as the reslurry diluent 240 (in which case, the filtrate 232 includes at least some liquid paraxylene), and a portion 244 of the filtrate 232 is recycled to the crystallizer 110 as a contributor to the liquid feedstream 204. The reslurry diluent 240 can be heated with a diluent heater 242, providing a heat input selected such that the resulting temperature of the solid-liquid slurry in the first reslurry drum 130 is adjusted to a desired value.

The filter cake 228 and a reslurry diluent 272 are then fed to the second reslurry drum 150 via a stream 248. Additionally, a paraxylene-rich feedstream having a paraxylene to total xylene isomer ratio of greater than 0.50 is also fed to the second reslurry drum 150. As shown in FIG. 3 the paraxylene-rich feedstream 310 may be combined with the filter cake 228 and reslurry diluent 272 before being fed to the second reslurry drum 150 via stream 248. Alternatively, the paraxylene-rich feedstream 310 may be fed directly to the second reslurry drum 150 i.e. via a separate stream (not shown).

Alternatively or additionally, one or more paraxylene-rich feedstreams having a paraxylene to total xylene isomer ratio of greater than 0.50 may be fed to the first crystallization/reslurry process 100 at other positions upstream of the second reslurry drum 150, for example in combination with the filter cake 212 fed to the first reslurry drum 130 via stream 220, and/or directly to the first reslurry drum 130 and/or to the crystallizer 110, either in combination with the paraxylene-lean feedstream 204 or through a separate stream (not shown).

The paraxylene-rich feedstream 310 may be obtained from any suitable source, including an effluent downstream of an STDP unit, a selective toluene alkylation unit or a second paraxylene recovery zone.

The second reslurry drum 150 operates analogously to the first reslurry drum 130, thus forming a reslurry effluent 252 including paraxylene crystals, liquid paraxylene and the liquid secondary component.

The reslurry effluent 252 is then fed to the final separation unit 160 in the illustrated embodiment of FIG. 3. The final separation unit 160 is a solid-liquid separator such as a filter column, a wash column or centrifuge. The separation unit 160 includes a filtrate 268 (similar to the other upstream filtrates 216 and 232) as a first output. The filtrate 268 is a liquid stream containing both liquid paraxylene and liquid secondary component, although it can include a small amount of paraxylene crystals. While the filtrate 268 can be discarded as a reject stream, it is preferably recycled for further processing. As illustrated in FIG. 3, a portion of the filtrate 268 is recycled to the second reslurry drum 150 as the reslurry diluent 272, and a portion 276 of the filtrate 268 is recycled to the first reslurry drum 130 as a contributor to the reslurry diluent 240. The reslurry diluent 272 can be heated with a diluent heater 274, providing a heat input selected such that the resulting temperature of the solid-liquid slurry in the reslurry drum 150 is adjusted to a desired value. The separation unit 160 also includes a product stream 256. A heater 170 preferably is used to melt any remaining paraxylene crystals in the product stream 256. A portion of the melted product stream 256 preferably is recycled to the separation unit 160 as a wash liquid 260, and a portion is withdrawn as a final product stream 264 that is a purified paraxylene stream having a paraxylene to total xylene isomer ratio greater than that of the paraxylene-rich feedstream 310. Preferably the wash liquid 260 and/or the final product stream 264 contains liquid paraxylene at a weight concentration of at least about 99.5 wt % (preferably at least about 99.7 wt %, more preferably at least about 99.8 wt %, for example about 99.9 wt %).

The yield of the disclosed process can be increased by recycling the filtrate from the crystallization stage separation unit 120 to a chemical reactor that can convert at least a portion of the liquid secondary component to paraxylene, which can then be recycled to the crystallization stage 105. For example, the filtrate 216 from the separation unit 120 may be recycled to an isomerization unit 180 (i.e. a chemical reactor) to convert the liquid secondary component (i.e. orthoxylene, metaxylene and/or ethylbenzene) to liquid paraxylene, thereby increasing the potential yield of the overall process 100.

As illustrated in FIG. 3, a paraxylene depleted filtrate 216 (e.g. including up to about 15 wt % paraxylene) and a hydrogen feed 280 are fed to the isomerization unit 180. A catalytic reaction in the isomerization unit 180 converts the inlet orthoxylene, metaxylene and/or ethylbenzene into paraxylene, and also generates heavier and lighter hydrocarbon components. The reaction products are separated in the distillation portion of the isomerization unit 180 to form a light hydrocarbon waste stream 288 (e.g. including C1 to C7 aliphatic and aromatic hydrocarbons), a heavy hydrocarbon stream 290 (e.g. including C9 and higher aliphatic aromatic hydrocarbons), and an isomerate 284. The isomerate stream 284 generally includes the following mixture of C8 aromatic hydrocarbons: about 20 wt % to about 25 wt % (e.g. about 22 wt %) paraxylene, about 15 wt % to about 30 wt % orthoxylene, about 40 wt % to 55 wt % metaxylene and about 5 wt % to about 15 wt % ethylbenzene. As illustrated in FIG. 3, the isomerate stream 284 may be mixed with a Mixed Xylene feed 292 to form a crystallization stage feed 296. The crystallization stage feed 296 and the recycle portion 244 of filtrate 232 are then combined to form the feedstream 204 to the crystallizer 110.

By feeding the paraxylene-rich feedstream 310 having a paraxylene to total xylene isomer ratio greater than 0.50 into the process 100, more paraxylene product is produced, but less feed is processed in the isomerization reactor 180, whilst the refrigeration duty used in the crystallizer 110 is not increased.

Figure 4:
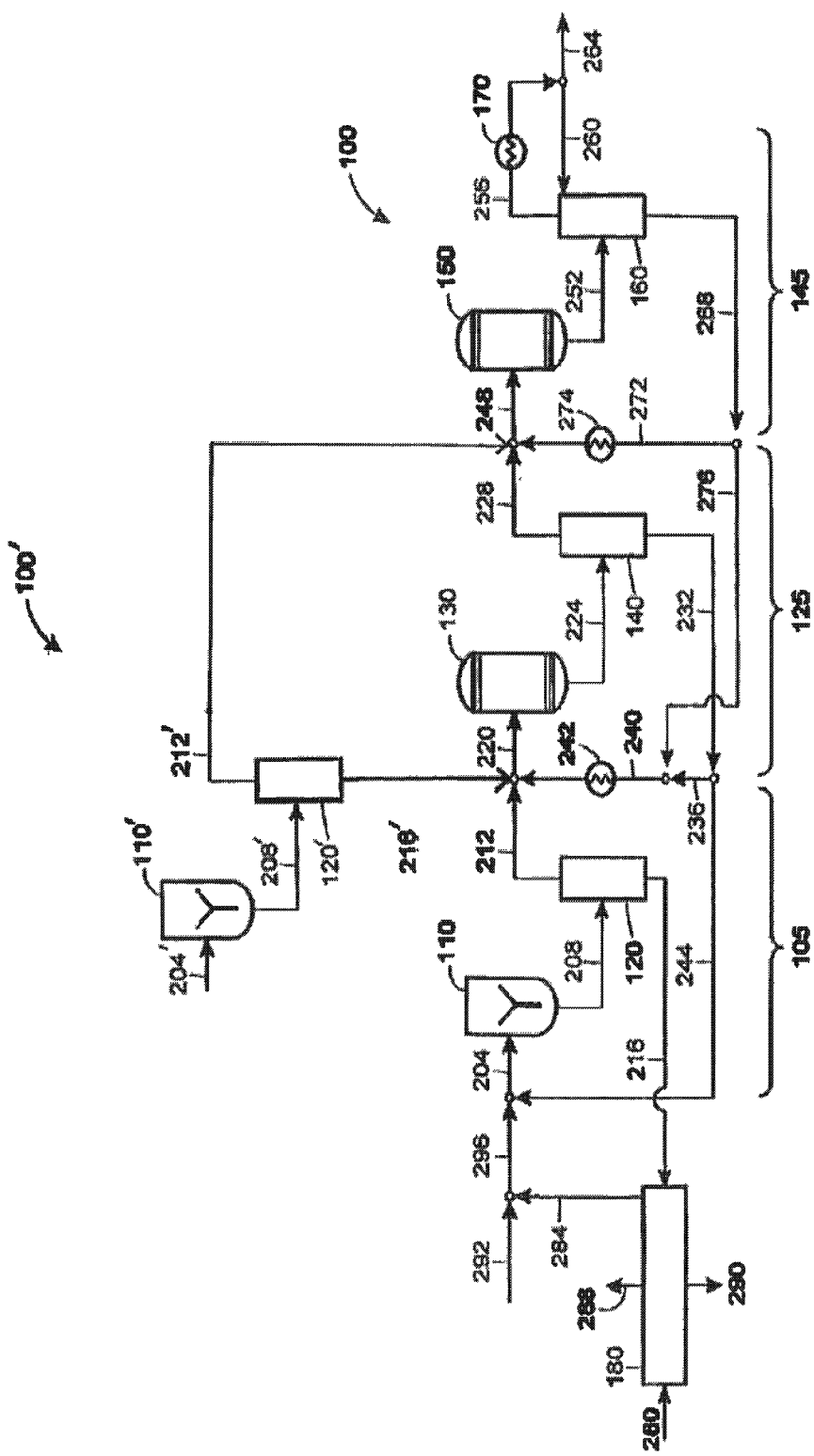
FIG. 4 is a process flow diagram illustrating an embodiment of the process including a first paraxylene recovery zone comprising crystallization and reslurry stages and a second paraxylene recovery zone comprising a crystallization stage.

FIG. 4 illustrates an additional embodiment of the disclosure, which includes a crystallization/reslurry process 100 and a crystallization/separation process 100'. The crystallization/reslurry process is carried out in a first paraxylene recovery zone 100 corresponding, in general, to the process illustrated in FIG. 3. The crystallization/separation step 100' is carried out in a crystallization unit.

As illustrated in FIG. 5, a paraxylene feedstream 204' is crystallized in crystallizer 110'. Paraxylene feedstream 204' may be obtained from any suitable source, and may be a paraxylene-lean feedstream or a paraxylene-rich feedstream, for example having a paraxylene to total xylene isomer ratio of 0.70 or lower. Crystallizer 110' is any suitable crystallization unit, but is suitably chilled by a high level refrigerant, such as propane, propylene or ammonia. Effluent 208' recovered from crystallization unit 110' is directed to a separator 120', which may be any suitable separator, such as a filter column, wash column or centrifuge. Effluent 208' is separated in separator 120' to form a paraxylene-rich cake 212' and a filtrate 216'. The paraxylene cake 212' is directed to the product reslurry drum 150 of paraxylene recovery zone 100, and at least a portion of the filtrate 216' is directed to the efficiency reslurry drum 130 and/or the crystallizer 110 of paraxylene recovery zone 100. Additionally, where a large volume of paraxylene-rich feed is available, a portion may be directed to crystallizer 110', whilst a further portion is sent directly to one or both of the efficiency stage and product stage reslurry drums 130 and 150 of paraxylene recovery zone 100.

EXAMPLE

Example 1 illustrates a process for the purification of paraxylene substantially in accordance with the present invention and FIG. 3.

The Example illustrates the separation of a paraxylene-lean feedstream in a paraxylene recovery zone substantially as illustrated in FIG. 3, with the addition of increasing proportions of a paraxylene-rich feedstream.

The paraxylene-lean feedstream had the following composition:

| | |
|---|---|
| Non-aromatics | 6.19 wt % |
| Benzene | 0.26 wt % |
| Toluene | 0.48 wt % |
| Ethylbenzene | 6.49 wt % |
| Paraxylene | 21.90 wt % |
| Metaxylene | 44.12 wt % |
| Orthoxylene | 20.02 wt % |
| Aromatic C9-plus | 0.54 wt % |

The paraxylene to total xylene isomer ratio of the paraxylene-lean feedstream was 0.25.

The paraxylene-rich feed stream had a paraxylene concentration of 95.00 wt % and the paraxylene to total xylene isomer ratio was 0.9588.

In all cases, the first stage refrigeration duty, which sets refrigeration compressor power was fixed at 0.03592 MMBTU (millions of BTU's) per thousand of pounds of paraxylene-lean feed. The duty of the efficiency stage reslurry heater was set at 0.0112 MMBTU/klb paraxylene-lean feed, and was fixed at this absolute amount for each run.

The paraxylene-rich feedstream was supplied at a temperature of 65° F. (18.3° C.).

Table 1 shows the effect of adding various amounts of paraxylene-rich feedstream to the product reslurry stage.

As shown in Table 1, a relative amount of 0.0621 paraxylene-rich feed can be fed to the product stage reslurry drum before the product stage diluent heater duty goes to 0. Below zero duty, would require additional refrigeration duty to maintain the same temperature in the product stage.

Even more paraxylene-rich feed could have been accommodated if this stream had been chilled below its 18.3° C. supply temperature.

And also shown in Table 1, a higher fraction (greater than 89%) of the paraxylene in the paraxylene-rich stream was recovered without a change in the first stage refrigeration duty. Furthermore, by feeding the paraxylene-rich feed to the product reslurry stage, the paraxylene production rate could be increased by about 38.4% without a change in the first stage refrigeration duty, and thus essentially without an increase in the ethylene and propane compressor power.

As a further benefit, the paraxylene reject filtrate rate dropped by about 4.2% when a relative proportion of 0.0621 paraxylene-rich feed was used. This could lead to lower isomerization and fractionation section utilities consumption, and in some arrangements could allow for even greater increases in paraxylene production.

| (1) Relative Amount of pX Rich Feed | Product Stage Diluent Heater Duty MMBTU/klb pX Product | (1) Relative Amount of pX Lean Feed | Relative 1$^{st}$ Stage Reject Rate | 1$^{st}$ Stage Reject Rate % Increase | (1) Relative pX Product Rate | Product Rate % Increase | Amount of pX in Imported Stream MPPH | Relative Amount of pX in pX Rich Stream | Additional pX Product MPPH | (2) Relative Amount of Additional pX Product | pX Recovery from pX Rich Stream % |
|---|---|---|---|---|---|---|---|---|---|---|---|
| 0 | 0.0335 | 1.000 | 0.8632 | 0.0 | 0.1368 | 0.0 | 0 | 0.000 | 0 | 1.000 | — |
| 0.0163 | 0.0223 | 0.988 | 0.8541 | −1.1 | 0.1506 | 10.1 | 19 | 0.015 | 17 | 1.101 | 89.4 |
| 0.0326 | 0.0132 | 0.976 | 0.8446 | −2.2 | 0.1644 | 20.2 | 38 | 0.031 | 34 | 1.202 | 89.2 |
| 0.0488 | 0.0054 | 0.964 | 0.8349 | −3.3 | 0.1781 | 30.2 | 57 | 0.046 | 51 | 1.302 | 89.1 |
| 0.0570 | 0.0020 | 0.958 | 0.8299 | −3.9 | 0.1850 | 35.2 | 67 | 0.054 | 59 | 1.352 | 89.0 |
| 0.0621 | 0.0000 | 0.954 | 0.8267 | −4.2 | 0.1893 | 38.4 | 73 | 0.059 | 65 | 1.384 | 89.0 |

Notes
(1) Amounts are relative to the pX lean feed rate for the base case
(2) Amounts are relative to pX product rate for base case

What is claimed is:

1. A process for recovering paraxylene from at least two feedstreams containing xylene isomers, comprising:
   directing to a paraxylene recovery zone a paraxylene-lean feedstream having a paraxylene to total xylene isomer ratio of 0.50 or less, the paraxylene recovery zone comprising at least one crystallization zone and at least one reslurry zone;
   directing to the paraxylene recovery zone a paraxylene-rich feedstream having a paraxylene to total xylene isomer ratio of greater than 0.50; and
   recovering from the paraxylene recovery zone a paraxylene containing product stream having a paraxylene to total xylene isomer ratio greater than that of the paraxylene-rich feedstream;
   wherein the at least one reslurry zone comprises at least one efficiency stage and a product stage downstream of the at least one efficiency stage, and at least a portion of the paraxylene-rich feedstream is directed to the product stage.

2. The process of claim 1, wherein at least a portion of the paraxylene-lean feedstream is directed to the at least one crystallization zone.

3. The process of claim 1, wherein at least one of the paraxylene-rich feedstream and the paraxylene-lean feedstream comprises at least a portion of an effluent downstream of a non-selective source of mixed xylenes.

4. The process of claim 3, wherein at least one of the paraxylene-rich feedstream and the paraxylene-lean feedstream comprises at least a portion of an effluent downstream of a refinery catalytic reformer.

5. The process of claim 3, wherein at least one of the paraxylene-rich feedstream and the paraxylene-lean feedstream comprises at least a portion of an effluent downstream of a non-selective toluene disproportionation unit.

6. The process of claim 3, wherein at least one of the paraxylene-rich feedstream and the paraxylene-lean feedstream comprises at least a portion of an effluent downstream of a non-selective toluene/aromatic C9 plus transalkylation unit.

7. The process of claim 3, wherein at least one of the paraxylene-rich feedstream and the paraxylene-lean feedstream comprises at least a portion of an effluent downstream of a non-selective aromatic C9 plus transalkylation unit or a non-selective methylation unit.

8. The process of claim 1, wherein the paraxylene-lean feedstream comprises at least a portion of an effluent downstream of an isomerization zone.

9. The process of claim 1, wherein the paraxylene-lean feedstream comprises at least a portion of an effluent downstream of a fractionation zone.

10. The process of claim 1 wherein the paraxylene-rich feedstream comprises at least a portion of an effluent downstream of a second paraxylene recovery zone.

11. The process of claim 10, wherein the second paraxylene recovery zone comprises at least one crystallization zone comprising at least one crystallizer.

12. The process of claim 11 wherein the least one crystallizer of the second paraxylene recovery zone is cooled by a high level refrigerant.

13. The process of claim 10, wherein the second paraxylene recovery zone comprises at least one crystallization zone and at least one reslurry zone.

14. The process of claim 10, wherein the second recovery zone comprises at least one selective adsorption zone.

15. The process of claim 1, wherein the paraxylene-lean feedstream has a ratio of paraxylene to total xylene isomers of 0.4 or less.

16. The process of claim 1, wherein the paraxylene-lean feedstream has a ratio of paraxylene to total xylene isomers of 0.15 to 0.5.

17. The process of claim 1, wherein the paraxylene-rich feedstream has a ratio of paraxylene to total xylene isomers of 0.55 or more.

18. The process of claim 1, wherein the paraxylene-rich feedstream has a ratio of paraxylene to total xylene isomers of 0.70 or more.

19. The process of claim 1, wherein the paraxylene-rich feedstream has a ratio of paraxylene to total xylene isomers of 0.80 or more.

20. The process of claim 1, wherein the paraxylene-rich feedstream has a ratio of paraxylene to total xylene isomers of 0.90 or more.

21. The process of claim 1, wherein the paraxylene containing product stream has a concentration of paraxylene of at least 99.0 wt %.

22. The process of claim 1, wherein the paraxylene containing product stream has a concentration of paraxylene of at least 99.5 wt %.

23. The process of claim 1, wherein the paraxylene containing product stream has a concentration of paraxylene of at least 99.7 wt %.

24. The process of claim 1, wherein at least a portion of the paraxylene-rich feedstream is directed to the at least one reslurry zone.

25. The process of claim 1, wherein at least a portion of the paraxylene-rich feedstream is cooled prior to its introduction to the product stage.

26. The process of claim 1, wherein at least a portion of the paraxylene-rich feedstream is cooled by a high level refrigerant.

27. The process of claim 1, wherein at least a portion of the paraxylene-rich feedstream is directed to the at least one crystallization zone.

28. The process of claim 27, wherein the at least one crystallization zone comprises at least two stages, and the paraxylene-rich feedstream is directed to a stage other than the first stage.

29. The process of claim 27, wherein at least a portion of the paraxylene-rich feedstream is cooled prior to its introduction to the at least one crystallization zone with a high level refrigerant.

30. The process of claim 27, wherein at least a portion of the paraxylene-rich feedstream is cooled prior to its introduction to the at least one crystallization zone with an indirect cooling medium.

31. The process of claim 30, wherein the indirect cooling medium comprises chilled water, or a chilled glycol solution.

32. The process of claim 30, wherein the indirect cooling medium comprises propane.

33. The process of claim 30, wherein the indirect cooling medium comprises propylene.

34. The process of claim 30, wherein the indirect cooling medium comprises ammonia.

35. The process of claim 12, wherein the high level refrigerant comprises propane.

36. The process of claim 12, wherein the high level refrigerant comprises propylene.

37. The process of claim 12, wherein the high level refrigerant comprises ammonia.

38. The process of claim 1, wherein at least a portion of the paraxylene-rich feedstream is cooled by chilled water or a chilled glycol solution.

39. The process of claim 26, wherein the high level refrigerant comprises propane.

40. The process of claim 26, wherein the high level refrigerant comprises propylene.

41. The process of claim 26, wherein the high level refrigerant comprises ammonia.

42. The process of claim 29, wherein the high level refrigerant comprises propane.

43. The process of claim 29, wherein the high level refrigerant comprises propylene.

44. The process of claim 29, wherein the high level refrigerant comprises ammonia.

45. The process of claim 1, wherein the paraxylene-rich feedstream comprises at least a portion of an effluent downstream of a selective source of mixed xylenes.

46. The process of claim 45, wherein the selective source of mixed xylene comprises a selective toluene disproportionation (STDP) unit.

47. The process of claim 45, wherein the selective source of mixed xylenes comprises a selective toluene alkylation unit.

* * * * *